United States Patent [19]

Chou et al.

[11] Patent Number: 5,606,048

[45] Date of Patent: Feb. 25, 1997

[54] STEREOSELECTIVE GLYCOSYLATION PROCESS FOR PREPARING 2'-DEOXY-2', 2'-DIFLUORONUCLEOSIDES AND 2'-DEOXY-2'-FLUORONUCLEOSIDES

[75] Inventors: Ta-Sen Chou, Indianapolis; Laurie M. Poteet, Zionsville; Douglas P. Kjell, West Lafayette, all of Ind.

[73] Assignee: Eli Lilly and Company, Lilly Corporate Center, Ind.

[21] Appl. No.: 340,972

[22] Filed: Nov. 17, 1994

Related U.S. Application Data

[63] Continuation-in-part of Ser. No. 44,309, Apr. 7, 1993, abandoned, which is a continuation-in-part of Ser. No. 902,302, Jun. 22, 1992, abandoned.

[51] Int. Cl.$^6$ .............................. C07H 1/00; C07H 19/00
[52] U.S. Cl. .................... 536/27.11; 536/27.12; 536/27.21; 536/27.6; 536/27.8; 536/27.81; 536/28.1; 536/28.3; 536/28.4; 536/28.5; 536/28.52; 536/28.53; 536/28.55; 536/28.54
[58] Field of Search ................ 536/27.21, 27.6, 536/27.61, 27.62, 27.8, 27.81, 28.5, 28.51, 28.52, 28.53, 28.54, 28.55, 27.11, 27.12

[56] References Cited

U.S. PATENT DOCUMENTS

| | | | |
|---|---|---|---|
| 3,282,921 | 11/1966 | Verheyden et al. | 260/211 |
| 3,721,664 | 3/1973 | Hoffer | 260/211.5 R |
| 4,145,531 | 3/1979 | Eckstein et al. | 536/26 |
| 4,182,859 | 1/1980 | Erhardt | 536/23 |
| 4,211,773 | 7/1980 | Lopez et al. | 424/180 |
| 4,526,988 | 7/1985 | Hertel | 549/313 |
| 4,625,020 | 11/1986 | Brundidge et al. | 536/18 |
| 4,751,221 | 6/1988 | Watanabe et al. | 514/46 |
| 4,965,374 | 10/1990 | Chou et al. | 549/313 |
| 5,175,267 | 12/1992 | Chu | 536/26.3 |
| 5,223,608 | 6/1993 | Chou et al. | 536/28.5 |
| 5,371,210 | 12/1994 | Chou | 536/27.11 |
| 5,401,838 | 3/1995 | Chou | 536/28.1 |
| 5,426,183 | 6/1995 | Kjell | 536/28.55 |

FOREIGN PATENT DOCUMENTS

| | | |
|---|---|---|
| 145978 | 6/1985 | European Pat. Off. |
| 211354 | 2/1987 | European Pat. Off. |
| 219829 | 4/1987 | European Pat. Off. |
| 339161 | 11/1989 | European Pat. Off. |
| 345751 | 12/1989 | European Pat. Off. |
| 428109 | 5/1991 | European Pat. Off. |
| 577303 | 1/1994 | European Pat. Off. |
| 2125401 | 3/1984 | United Kingdom . |

OTHER PUBLICATIONS

Vorbruggen, et al., *J. Org. Chem.*, 41, 2084 (1976).
Hubbard, et al., *Nucleic Acid Research*, 12, 6827 (1984).
R. P. Hodge, et al., *J. Org, Chem.*, 56, 1553–64 (1991).
Tann, et al., *J. Org. Chem.*, 50, 3644 (1985).
Howell, et al., *J. Org. Chem.*, 53, 85 (1988).
Hoffer, et al., *Chem. Ber.*, 93, 2777–81 (1960).

*Primary Examiner*—James O. Wilson
*Attorney, Agent, or Firm*—Margaret M. Brumm; Joseph A. Jones; David E. Boone

[57] ABSTRACT

A stereoselective glycosylation process for preparing beta- and alpha-anomer enriched 2'-deoxy-2',2'-difluoronucleosides and 2'-deoxy-2'-fluoronucleosides by reacting a concentrated alpha- or beta-anomer enriched 2-deoxy-2,2-difluorocarbohydrate or 2-deoxy-2-fluorocarbohydrate with at least a molar equivalent of a nucleobase derivative in a high boiling inert solvent.

38 Claims, No Drawings

STEREOSELECTIVE GLYCOSYLATION PROCESS FOR PREPARING 2'-DEOXY-2', 2'-DIFLUORONUCLEOSIDES AND 2'-DEOXY-2'-FLUORONUCLEOSIDES

CROSS REFERENCE TO RELATED APPLICATION

This application is a continuation-in-part of Ser. No. 08/044,309, filed Apr. 7, 1993, now abandoned, which is a continuation-in-part of Ser. No. 07/902,302, filed Jun. 22, 1992, now abandoned.

BACKGROUND OF THE INVENTION

1. Field of the Invention

The invention pertains to the field of pharmaceutical chemistry and provides a stereoselective glycosylation process for preparing 2'-deoxy-2',2'-difluoronucleosides and 2'-deoxy-2'-fluoronucleosides.

2. State of the Art

The continued interest in the synthesis of 2'-deoxynucleosides and their analogues is reflected in their successful use as therapeutic agents in viral and cancerous diseases. A critical step in the synthesis of 2'-deoxynucleosides is the condensation of the nucleobase and carbohydrate to form the N-glycosidic bond. When the carbohydrate possesses a 2-hydroxy substituent, the substituent provides a substantial degree of 1,2-anchiomeric assistance, which facilitates stereoselective glycosylation. However, processes for synthesizing of 2'-deoxynucleosides are typically non-stereoselective and form a mixture of alpha and beta nucleosides.

Vorbruggen, et al., *J. Org. Chem.*, 41, 2084 (1976) provided an outstanding development in the field of glycosylation and showed how nucleosides may be obtained from the Friedel-Crafts catalyzed reaction of a peracylated carbohydrate and silylated heterocycles in a solvent such as 1,2-dichloroethane or acetonitrile. But when this process was applied to the synthesis 2'-deoxynucleosides, a 1:1 alpha to beta-anomeric mixture of nucleoside products was produced.

Some deoxynucleosides have been prepared in high yield from deoxyhalogenose with Friedel-Crafts catalysts, notably, 1-chloro-2-deoxy-3,5-di-p-toluoyl-alpha-D-erythropentofuranose, see, M. Hofer, *Chem. Ber,* 93, 2777 (1960). However, halogenoses are less stable thermally than peracylated carbohydrates and produce a 1:1 alpha to beta-anomeric mixture of nucleoside products. Walker, et al., *Nucleic Acid Research,* 12, 6827 (1984), used halogenose in condensation reactions to study the factors controlling the anomeric ratio of nucleoside products and found that beta-anomer nucleosides were formed exclusively from alpha-halo-carbohydrates via $S_N2$ displacement. The corresponding alpha-anomer nucleoside contamination was determined to result from the anomerization of alpha-halo carbohydrate to beta-halo carbohydrate before the $S_N2$ displacement reaction. Walker, et al., found that by changing the solvent or catalyst higher yields of the desired beta-anomer nucleoside were produced.

R. P. Hodge et. al., *J. Org. Chem.*, 56, 1553 (1991), described preparing pyrimidine and purine nucleosides containing deuterium at the C-1' position by the method described by Walker, et al. 1'-Deuterium-2'-deoxycytidine was prepared by reacting a carbohydrate and silylated cytosine derivative but the reaction gave poor yields. However, the yield was significantly improved when silylated uridine derivatives were used.

The synthesis of 2'-deoxy-2'-fluoronucleosides advanced rapidly when a procedure for synthesizing 2-deoxy-2-fluoro-3,5-di-O-benzoyl-alpha-D-arabinosyl bromide was made avail. able; see Tann, et. al., *J. Org. Chem.*, 50, 3644 (1985) and Howell, et. al., *J. Org. Chem.*, 53, 85 (1988). It was discovered that 2-deoxy-2-fluoro-3,5-di-O-benzoylalpha-D-arabinosyl bromide did not anomerize in dry acetonitrile over extended periods. Therefore, high yields of beta-nucleosides could be obtained from 2-deoxy-2-fluoro-3,5-di-O-benzoyl-alpha-O-arabinosyl bromide via $S_N2$ displacement. Also, stereoselectivity of the nucleoside products could be achieved if either carbon tetrachloride or chloroform solvents was employed.

The formation of the N-glycoside bond in 2'-deoxy-2',2'-difluoronucleoside synthesis is much more difficult than in instances where the carbohydrate is 1,2-anchiomerically assisted or contains only 1 fluorine at the C-2 position. The traditional carbohydrate leaving groups, such as those used in the Vorbruggen condensation method, acetate, chloride and bromide, render the carbohydrate inactive. In order to overcome this problem, Hertel, U.S. Pat. No. 4,526,988, described a modified version of the Vorbruggen condensation method that relied on more reactive sulfonate leaving groups attached to the carbohydrate to affect its reactivity. For example, hydroxy protected carbohydrates, such as 2-deoxy-2,2-difluoro-D-ribofuranose, containing a methanesulfonate, toluenesulfonate, ethanesulfonate, isopropanesulfonate or 4-methoxybenzenesulfonate leaving group at the C-1 position, were reacted with a protected nucleobase at temperatures of 50° C. to 220° C., in the presence of a high boiling solvent, such as dimethylformamide, dimethylacetamide and hexamethylphosphoramide. Hertel teaches that when carrying out the glycosylation reaction at elevated pressures, any convenient inert solvent, such as ethers, halogenated alkanes, and aromatics, can be used since the elevated pressure eliminates the loss of low boiling inert solvents due to evaporation. However, at reaction temperatures from room temperature to 100° C., a catalyst such as trifluoromethane-sulfonyloxysilane is required.

U.S. Pat. No. 4,965,374, Chou, et al., reports that Hertel's condensation method provides alpha-anomer stereoselectively and therefore produces a 4:1 alpha to beta anomer ratio of nucleoside products and goes on to describe an improved procedure, based on the Vorbruggen condensation method, that employs a pivotol intermediate of 2-deoxy-2, 2-difluoro-3,5-di-O-benzoyl-alpha-D-arabinosyl methanesulfonate. However, Chou's condensation method forms a 1:1 alpha to beta anomer mixture of nucleoside products.

Despite the processing advances in nucleoside synthesis, there continues to be a need for a stereoselective glycosylation process capable of efficiently producing beta- or alpha-anomer enriched 2'-deoxy-2',2'-difluoronucleosides and 2'-deoxy-2'-fluoronucleosides in increased yields in the absence of a catalyst.

Accordingly, one object of the present invention is to provide a stereoselective glycosylation process for efficiently preparing beta- or alpha-anomer enriched 2'-deoxy-2',2'-difluoronucleosides and 2'-deoxy-2'-fluoronucleosides.

Another object of the present invention is to provide a stereoselective glycosylation process for preparing beta- or alpha-anomer enriched 2'-deoxy-2',2'-difluoronucleosides and 2'-deoxy-2'-fluoronucleosides without the use of a catalyst.

Another object of the present invention is to provide a stereoselective glycosylation process for preparing beta- or alpha-anomer enriched 2'-deoxy-2',2'-difluoronucleosides and 2'-deoxy-2'-fluoronucleosides in yields higher than those produced by conventional glycosylation procedures.

Yet another object of the present invention is to provide a stereoselective glycosylation process for preparing beta- or alpha-anomer enriched 2'-deoxy-2',2'-difluoronucleosides and 2'-deoxy-2'-fluoronucleosides offering a means for isolating beta- or alpha-anomer enriched nucleosides in the form of a crude product or an acid addition salt such as a hydrochloride salt.

Other objects and advantages of the present invention will become apparent from the following description of embodiments.

SUMMARY OF THE INVENTION

The invention is a stereoselective glycosylation process for preparing a beta-anomer enriched nucleoside of the formula

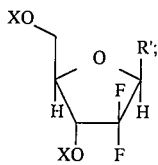
(IB)

wherein each X is independently selected from hydroxy protecting groups and R' is a nucleobase selected from the group consisting of

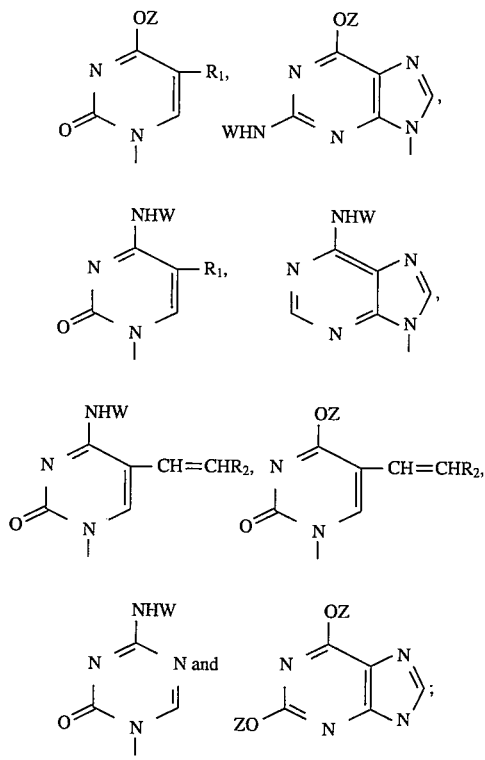

wherein $R_1$ is selected from the group consisting of hydrogen, alkyl and halo; $R_2$ is selected from the group consisting of hydrogen, alkyl and halo; Z is a hydroxy protecting group; and W is an amino protecting group; comprising reacting a concentrated alpha-anomer enriched 2,2-difluorocarbohydrate of the formula

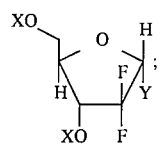
(IIA)

wherein Y is selected from the group consisting of alkylsulfonyloxy, arylsulfonyloxy, substituted alkylsulfonyloxy and substituted arylsulfonyloxy and X is as defined above; with at least a molar equivalent of a nucleobase derivative, R", selected from the group consisting of

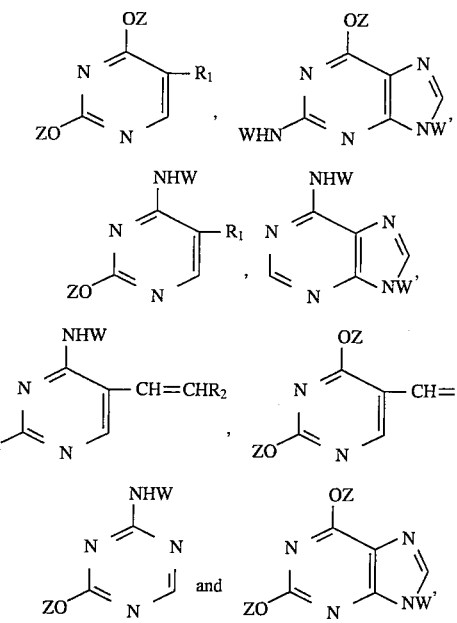

wherein $R_1$, $R_2$, Z and W are as defined above; in a high boiling inert solvent.

In another aspect the invention is a stereoselective glycosylation process for preparing an alpha-anomer anomer enriched nucleoside of the formula

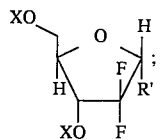
(IA)

wherein X and R' are as defined above; comprising reacting a concentrated beta-anomer enriched 2,2-difluorocarbohydrate of the formula

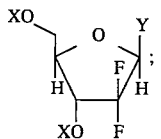
(IIB)

wherein X and Y are as defined above; with at least a molar equivalent of a nucleobase derivative, R", wherein R" is as defined above, in a high boiling inert solvent.

In another aspect the invention is a stereoselective glycosylation process for preparing a betaanomer enriched nucleoside of the formula

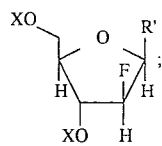  (IVB)

wherein X and R' are as defined above; comprising reacting a concentrated alpha-anomer enriched 2-fluorocarbohydrate of the formula

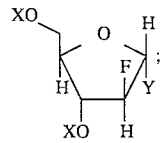  (VA)

wherein Y and X are as defined above; with at least a molar equivalent of a nucleobase derivative, R", wherein R" is as defined above, in a high boiling inert solvent.

In another aspect the invention is a stereoselective glycosylation process for preparing an alpha-anomer enriched nucleoside of the formula

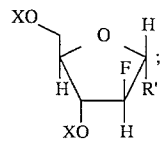  (IVA)

wherein X and R' are as defined above; comprising reacting a concentrated beta-anomer enriched 2-fluorocarbohydrate of the formula

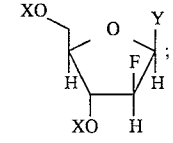  (VB)

wherein X and Y are as defined above; with at least a molar equivalent of a nucleobase derivative, R", wherein R" is as defined above, in a high boiling inert solvent.

The invention also provides a stereoselective glycosylation process for preparing a beta-anomer enriched nucleoside of the formula

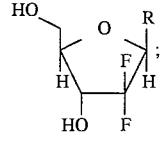  (VIB)

wherein R is a deblocked nucleobase selected from the group consisting of

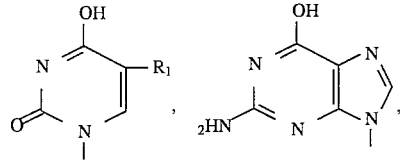

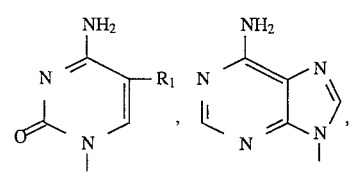

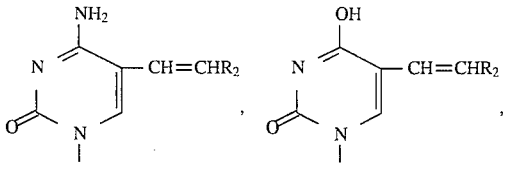

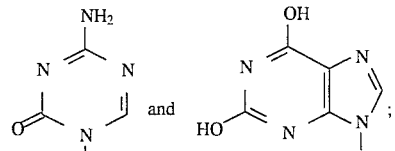

wherein $R_1$ is selected from the group consisting of hydrogen, alkyl and halo; $R_2$ is selected from the group consisting of hydrogen, alkyl and halo; comprising reacting a concentrated alpha-anomer enriched 2,2-difluorocarbohydrate of the formula

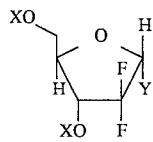  (IIA)

wherein Y is selected from the group consisting of alkylsulfonyloxy, arylsulfonyloxy, substituted alkylsulfonyloxy and substituted arylsulfonyloxy and each X is a hydroxy protecting group; with at least a molar equivalent of a nucleobase derivative, R", selected from the group consisting of

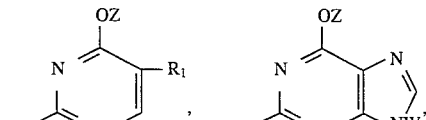

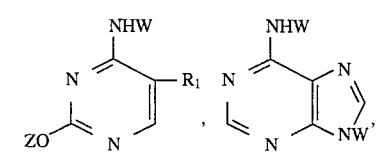

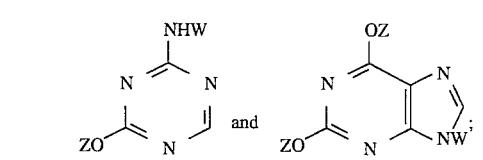

wherein $R_1$ and $R_2$ are as defined above; Z is a hydroxy protecting group; W is an amino protecting group; in a high boiling inert solvent; and deblocking.

Also provided is a stereoselective glycosylation process for preparing an alpha-anomer enriched nucleoside of the formula

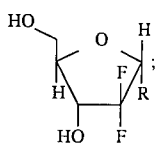 (VIA)

wherein R is a deblocked nucleobase as defined above; comprising reacting a concentrated beta-anomer enriched 2,2-difluorocarbohydrate of the formula

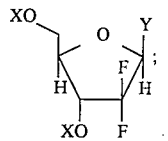 (IIB)

wherein Y is selected from the group consisting of arylsulfonyloxy and substituted arylsulfonyloxy and each X is a hydroxy protecting group; with at least a molar equivalent of a nucleobase derivative, R'', wherein R'' is as defined above; in a high boiling inert solvent; and deblocking.

Also provided is a stereoselective glycosylation process for preparing a beta-anomer enriched nucleoside of the formula

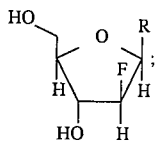 (VIIB)

wherein R is a deblocked nucleobase as defined above; comprising reacting a concentrated alpha-anomer enriched 2-fluorocarbohydrate of the formula

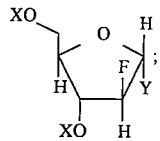 (VA)

wherein Y is selected from the group consisting of alkylsulfonyloxy, arylsulfonyloxy, substituted alkylsulfonyloxy and substituted arylsulfonyloxy and each X is a hydroxy protecting group; with at least a molar equivalent of a nucleobase derivative, R'', wherein R'' is as defined above; in a high boiling inert solvent; and deblocking.

Finally, provided is a stereoselective glycosylation process for preparing an alpha-anomer enriched nucleoside of the formula

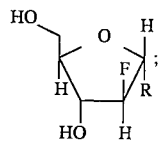 (VIIA)

wherein R a deblocked nucleobase as defined above; comprising reacting a concentrated beta-anomer enriched 2-fluorocarbohydrate of the formula

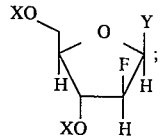 (VB)

wherein Y is selected from the group consisting of arylsulfonyloxy and substituted arylsulfonyloxy and each X is a hydroxy protecting group; with at least a molar equivalent of a nucleobase derivative, R'', wherein R'' is as defined above; in a high boiling inert solvent; and deblocking.

DETAILED DESCRIPTION OF THE INVENTION

Throughout this document, all temperatures are in degress Celcius, all proportions, percentages and the like are in weights and units and all mixtures are in volume units, except where otherwise indicated. Anomeric mixtures are expressed as a weight/weight ratio or as a percent. The term "lactol" alone or in combination refers to a 2-deoxy-2,2-difluoro-D-ribofuranose or 2-deoxy-2-fluoro-D-ribofuranose. The term "xylenes" alone or in combination refers to all isomers of xylene and mixtures thereof. The term "carbohydrate" alone or in combination refers to an activated lactol wherein the hydroxy group at the C-1 position has been replaced by a desirable leaving group. The term "halo" alone or in combination refers to chloro, iodo, fluoro and bromo. The term "alkyl" alone or in combination refers to straight, cyclic and branched chain aliphatic hydrocarbon groups which preferably contain up to 7 carbon atoms, such as methyl, ethyl, n-propyl, isopropyl, n-butyl, t-butyl, n-pentyl, n-hexyl, 3-methylpentyl groups and the like or substituted straight, cyclic and branched chain aliphatic hydrocarbons, such as chloroethyl, 1,2-dichloroethyl, and the like. The term "alkoxy" alone or in combination refers to compounds of the general formula AO; wherein A is alkyl. The term "aryl" alone or in combination refers to carbocyclic or heterocyclic groups such as phenyl, naphthyl, thienyl and substituted derivatives thereof. The term "aromatic" alone or in combination refers to benzene-like structures containing $(4n+2)$ delocalized $\pi$ electrons. The terms "sulfonate" or "sulfonyloxy" alone or in combination refer to compounds of the general formula $BSO_3$; wherein B is alkyl or aryl. The term "substituted" alone or in combination refers to a substitution by one or more of the groups selected from cyano, halo, carboalkoxy, toluoyl, nitro, alkoxy, alkyl, and dialkylamino. The phrase "anomer-enriched" alone or in combination refers to an anomeric mixture wherein the ratio of a specified anomer is greater than 1:1 and includes substantially pure anomer. The term "concentrated" alone or in combination refers to a solution wherein the weight of carbohydrate dissolved in solvent is greater than 20 percent by weight per unit volume of solvent. For example, dissolving 100 grams of carbohydrate in 200 milliliters of solvent would form a 50 percent carbohydrate solution.

In accordance with the present glycosylation process, beta- and alpha-anomer enriched 2'-deoxy-2',2'-difluoronucleosides and 2'-deoxy-2'-fluoronucleosides of formulas I and IV are prepared by reacting a concentrated alpha- or beta-anomer enriched carbohydrate of formulas II and V with at least a molar equivalent of a nucleobase derivative in a high boiling inert solvent as shown in the following reaction schemes for making beta-anomer enriched nucleosides:

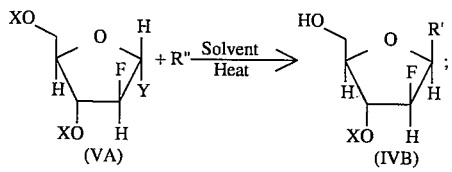

and

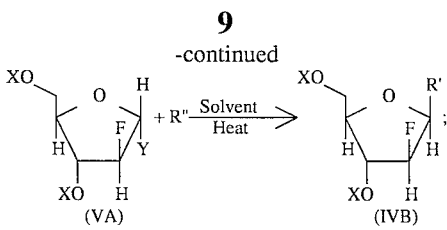

wherein Y, X, R" and R' see as defined above. While not wishing to be bound by theory, it is believed that the glycosylation reaction proceeds primarily via $S_N2$ displacement. Therefore, the beta-anomer enriched nucleoside products are derived from alpha-anomer enriched carbohydrates. Conversely, the alpha-anomer enriched nucleoside products are derived from beta-anomer enriched carbohydrates.

The lactol starting materials suitable for use in the present glycosylation process are commonly known in the art and can be readily synthesized by standard procedures commonly employed by those of ordinary skill in the art. For example, U.S. Pat. No. 4,526,988 teaches the synthesis of 2,2-difluoro-2-deoxy-D-ribofuranoses having the formula

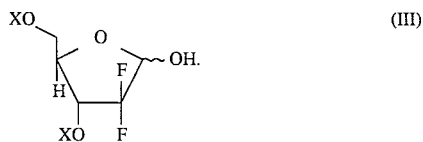

In addition, Reichman, et al., *Carbohydro. Res.*, 42, 233 (1975) teaches the synthesis of 2-deoxy-2-fluoro-D-ribofuranoses of the formula

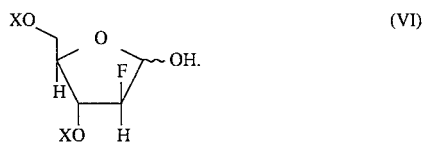

In a preferred embodiment, a 2,2-difluoro-2-deoxy-D-ribofuranose-3,5-dibenzoate of formula III is used to prepare the blocked nucleoside products under the present invention.

Glycosylation reactions typically require protecting the oxygen atoms of the hydroxy groups of the lactol of formulas III and VI to prevent the hydroxy groups from reacting with the nucleobase derivative, or being decomposed in some manner. Hydroxy protecting groups (X) suitable for use in the present glycosylation process may be chosen from known protecting groups used in synthetic organic chemistry. Each hydroxy protecting group selected is preferably capable of being efficiently placed on the lactol and easily removed therefrom once the glycosylation reaction is completed. Hydroxy protecting groups known in the art are described in Chapter 3 of *Protective Groups in Organic Chemistry*, McOmie Ed., Plenum Press, New York (1973), and Chapter 2 of *Protective Groups in Organic Synthesis*, Green, John, J. Wiley and Sons, New York (1981); preferred are ester forming groups such as formyl, acetyl, substituted acetyl, propionyl, butynyl, pivaloyl, 2-chloroacetyl, benzoyl, substituted benzoyl, phenoxycarbonyl, methoxyacetyl; carbonate derivatives such as phenoxycarbonyl, ethoxycarbonyl, t-butoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkylsilyl and 1,1,3,3-tetraisopropyldisloxanyl; carbamates such as N-phenylcarbamate and N-imidazoylcarbamate; however more preferred are benzoyl, mono-substituted benzoyl and disubstituted benzoyl, acetyl, pivaloyl, triphenylmethyl ethers, and silyl ether forming groups, especially t-butyldimethylsilyl; while most preferred is benzoyl.

In attaching each hydroxy protecting group to the lactol, typical reaction conditions are employed and depend on the nature of the protecting group chosen. Suitable reaction conditions are discussed in U.S. Pat. No. 4,526,988 which is incorporated herein by reference.

To obtain an efficient reaction of the nucleobase derivative and carbohydrate, an appropriate leaving group is stereoselectively attached to the lactol of formulas III and VI which activates the lactol and generates the beta- and alpha-anomer enriched carbohydrate of formulas II and V. The leaving group (Y) off the carbohydrate may be selected from the group consisting of alkylsulfonyloxy, arylsulfonyloxy, substituted alkylsulfonyloxy and substituted arylsulfonyloxy; provided that trifluoromethanesulfonyloxy, 1,1,1-trifluoroethanesulfonyloxy, octafluorobutanesulfonyloxy ($C_4F_8HSO_2$) and nanofluorobutanesulfonyloxy ($C_4F_9SO_2$) are not used; however, more preferred are methanesulfonyloxy, 2-chloroethanesulfonyloxy, toluenesulfonyloxy, p-nitrobenzenesulfonyloxy, 2,4-dinitrobenzenesulfonyloxy and p-bromobenzenesulfonyloxy; while most preferred is methanesulfonyloxy.

The alpha-anomer enriched carbohydrate of formula II may be prepared by one of two methods. The alpha-anomer enriched carbohydrate of formula V is prepared by the second of these methods. The first method is described in U.S. Pat. No. 5,256,798, and teaches treating a beta-anomer ribofuranosyl sulfonate or anomeric mixture thereof with a source of a conjugate anion of a sulfonic acid at elevated temperatures in an inert solvent. The second method is described in pending allowed U.S. Pat. application Ser. No.07/902,301, Attorney Docket X-8623, and teaches reacting the lactol of formulas III and VI with an amine base such as triethylamine, triethylamine, tributylamine, dibutylamine, diethylmethylamine, dimethylethylamine, benzylmethylamine, N-methylmorpholine, tripropylamine, dipropylethylamine, N,N-dimethylbenzylamine, dimethylbenzylamine, diisopropylethylamine, diethylamine, 1,8-diazabicyclo[5.4.0]undec-7-ene and 1,5-diazabicyclo[4.3.0]non-5-ene. The amine base preferably has a pKa of from about 8 to about 20 and is employed in a range of from about 1 molar equivalent to about 2 molar equivalents and more preferably from about 1.2 molar equivalents to about 1.5 molar equivalents. The reaction is carried out in an inert solvent having a freezing point temperature preferably below −78° C. Preferred solvents are selected from the group consisting of dichloromethane, 1,2-dichloroethane, dichlorofluoromethane, acetone, toluene, anisole, chlorobenzene, and mixtures thereof. The temperature of the solvent mixture is adjusted preferably in the range from about −40° C. to about −120° C. and more preferably below about −78° C. While not wishing to be bound by theory it is believed that the low temperature shifts the alpha to beta anomeric ratio of the lactol in favor of the alpha-anomer in a range from about 2:1 to about 4:1 alpha to beta. For example, a compound of formula III, where X is benzoyl, was added to dichloromethane and triethylamine at room temperature for 30 minutes. Next, the temperature of the reaction solvent was lowered. An $^{19}F$ NMR, taken at various temperatures, shows an increase in the alpha to beta ratio of the ionized lactol as the temperature was lowered:

| Temperature | Alpha/Beta Ratio |
| --- | --- |
| 19° C. | 2.0:1 |
| −3° C. | 2.3:1 |
| −23° C. | 2.5:1 |
| −43° C. | 3.0:1 |
| −63° C. | 3.6:1 |
| −83° C. | 4.4:1 |

The ionized lactol is then trapped in solution at the low temperature and higher alpha-anomer ratio by adding a sulfonating reagent which forms an alpha-anomer enriched carbohydrate.

The sulfonating reagents are selected from the group consisting of substituted and unsubstituted alkyland arylsulfonyl halides and sulfonic acid anhydrides, depending on the leaving group desired.

A method for preparing the beta-anomer enriched carbohydrates of formula II is described in U.S. Pat. No. 5,252,756. The method requires reacting a lactol of formula III with an arylsulfonyl halide or arylsulfonyl anhydride such as toluenesulfonyl chloride, benzenesulfonyl chloride and p-bromobenzenesulfonyl chloride, in the presence of an amine base such as triethylamine.

The beta- or alpha-anomer enriched carbohydrates may be isolated in substantially pure form; i.e., greater than 95 percent purity; by the procedure described in U.S. Pat. No. 5,256,797. The method involves warming an anomeric mixture of the carbohydrates in a solvent from about 30° C. to about 70° C. to form a supersaturated solution. The solvent may be selected from the group consisting of 1,2-chloroethane, anisole, glyme, and mixtures thereof. The carbohydrate forms a precipitate when the temperature of the solution is lowered and a counter solvent is added. The counter solvent may be selected from the group consisting of methanol, ethanol, toluene, ether, dichloromethane, and mixtures thereof. The resulting carbohydrate crystals are then recovered from the solution and dried.

The nucleobases (R") employed herein are commonly known to organic chemists and no discussion of their synthesis is necessary. However, in order to be useful in the present glycosylation process, the nucleobase derivatives or their tautomeric equivalents bearing amino or hydroxy groups preferably contain protecting groups such as primary amino protecting groups (W) and/or hydroxy protecting groups (Z), depending on the nature of the nucleobase drivative selected. The protecting group blocks the hydroxy or amino groups which may provide a competing reaction site for the beta- or alpha-anomer carbohydrate. The protecting groups are attached to the nucleobase derivative (R") which is reacted with the beta-or alpha-anomer enriched carbohydrate of formulas II and V and are removed subsequent thereto. A procedure :for protecting nucleobase derivatives is described in U. S. Pat. No. 4,526,988.

Preferred amino protecting groups (W) for pyrimidine nucleobase derivatives are selected from the group consisting of silyl ether forming groups such as trialkylsilyl, t-butyldialkylsilyl and t-butyldiarylsilyl; carbamates such as t-butoxycarbonyl, benzyloxycarbonyl, 4-methoxybenzyloxycarbonyl, and 4-nitrobenzyloxycarbonyl; formyl, acetyl, benzoyl and pivalamido; ether forming groups such as methoxymethyl, t-butyl, benzyl, allyl and tetrahydropyranyl; more preferred is trimethylsilyl. Preferred amino protecting groups (W) for purine nucleobase derivatives are selected from the group consisting of alkylcarboxamides, haloalkylcarboxamides and arylcarboxamides such as 2-trialkylsilylethoxymethyl, 4-methoxybenzyl, 3,4-dimethoxybenzyl, t-butyl, phthalamido, tetrahydropyranyl, tetrahydrofuranyl, methoxymethyl ether, methoxythiomethyl, trityl, pivalamido, t-butyldimethylsilyl, t-hexyldimethylsilyl, triisopropylsilyl, trichloroethoxycarbonyl, trifluoroacetyl, naphthoyl, formyl, acetyl; sulfonamides such as alkylsulfonamido and arylsulfonamido, and more preferred is pivalamido. Besides serving as an amino protecting group, the pivalamido protecting group increases the solubility of notoriously insoluble purine nucleobase derivatives and directs the N-glycosidic coupling of the purine bases to the 9 regioisomer as opposed to the 7 regioisomer.

Preferred hydroxy protecting groups (Z) for pyrimidine nucleobase derivatives are selected from silyl ether forming groups such as trialkylsilyl; carbamates such as t-butoxycarbonyl, benzyloxycarbonyl, 4-methoxybenzyloxycarbonyl and 4-nitrobenzyloxycarbonyl; carbocyclic esters such as formyl, acetyl, and pivalamido; preferred is trimethylsilyl. Preferred hydroxy protecting groups (Z) for purine nucleobase derivatives are selected from the group consisting of ether forming groups such as benzyl, t-butyl, trityl, tetrahydropyranyl, tetrahydrofuranyl, methoxymethyl, trityl; esters such as formyl, acetylpropionyl, pivalamido, benzoyl, substituted benzoyl; carbonates such as carbobenzoxy, L-butoxycarbonyl, carbethoxy, vinyloxycarbonyl; carbamates, such as N,N-dialkylcarbamoyl; trialkylsilyl ethers such as t-butyltrimethylsilyl, t-hexyldimethylsilyl, triisopropylsilyl; more preferred is pivalamido.

In providing protecting groups to the nucleobase derivatives of the present process, the protecting group itself may be protected. For example, N-acetylcytosine may be protected with trimethylsilyl to give bistrimethylsilyl-N-acetylcytosine.

In addition, it is often advisable to convert any keto oxygen atoms on the nucleobase derivative to enol form. This makes the nucleobase derivative more aromatic and enhances the reactivity of the nucleobase derivative with the alpha-anomer enriched carbohydrate of formulas II and V. It is most convenient to enolize the keto oxygens and provide silyl protecting groups for them. In a preferred embodiment of the present process, the nucleobase derivative (R") employed is of the formula

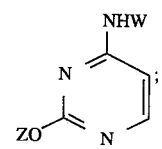

wherein Z and W are trimethylsilyl.

In the present process we have found that a carbohydrate solution of at least 20 percent carbohydrate is essential in providing a stereoselective yield of beta- or alpha-anomer enriched nucleoside products in the absence of a catalyst. Therefore, tile amount of carbohydrate employed in the present process must be sufficient to provide at least a 20 percent carbohydrate concentration in the reaction mixture. However, the carbohydrate concentration preferably ranges from about 20 percent to about 70 percent; more preferably from about 30 percent to about 70 percent; and most preferably from about 30 percent to about 50 percent.

The solvent used to prepare the nucleobase derivative may be removed prior to the glycosylation reaction or admixed with the reaction solvent, provided the admixture is inert to the glycosylation reaction.

The reaction solvent suitable for use in present process must be inert to the glycosylation reaction conditions and have a boiling point above about 70° C. Preferred reaction solvents are selected from the group consisting of aromatic, haloalkyl, alkoxy- and halosubstituted aromatic solvents, and mixtures thereof such as 1,2-dichloroethane, 1, 1,2-trichloroethane, glyme, diglyme, toluene, xylenes, anisole, dichlorobromomethane, chlorobenzene, dibromochloromethane, tribromomethane, dibromomethane, and mixtures thereof; more preferred are anisole, toluene, xylenes and mixtures thereof; and most preferred is anisole.

In accordance with the present process, the nucleobase derivative (R") must be employed in an equimolar amount, relative to the amount of carbohydrate employed. However, it is more preferable to use an excess of nucleobase derivative ranging from about 3 molar equivalents to 30 molar equivalents; more preferably from about 10 molar equivalents to 20 molar equivalents; and most preferably from about 15 molar equivalents to about 20 molar equivalents. In preparing the alpha-anomer enriched nucleosides by the present process a smaller amount of nucleobase derivative may be employed ranging from about 1.5 molar equivalents to about 10 molar equivalents.

Although not critical, it is advisable that the reaction between the beta- and alpha-anomer enriched carbohydrate of formulas II and V and the nucleobase derivative be carried out in a dry atmosphere, e.g. in dry air, nitrogen or argon. This is because certain nucleobase derivatives such as silylated nucleobase derivatives are moisture sensitive.

The glycosylation reaction temperature employed in the present process is from about 70° C. to about 170° C.; however, about 80° C. to about 150° C. is more preferred; while about 100° C. to about 130° C. is most preferred. The glycosylation reaction is preferably carried out under atmospheric conditions and is substantially complete in about 30 minutes to about 20 hours.

The progress of the present process may be followed by procedures well known to one of ordinary skill in the art such as high pressure liquid chromatography (HPLC) or thin layer chromatography (TLC) which can be used to detect the presence of the nucleoside product.

In accordance with the present process, the beta-anomer enriched nucleosides are prepared in an alpha to beta anomeric ratio greater than 1:1 to about 1:9. On the other hand, the alpha-anomer enriched nucleosides of formulas I and IV are prepared in a beta to alpha anomeric ratio from about 1:1 to about 1:20.

An unusual process of isolation and purification has been found to be advantageous, when preparing the compound of Formula IB wherein the nucleobase is blocked cytosine. The process proceeds as follows. When the glycosylation reaction has proceeded as far as is desired, the reaction mixture is diluted with an organic solvent. Acceptable solvents are from the classes of ethers, esters, and nitriles; preferred examples are acetonitrile, ethyl acetate and tetrahydrofuran. The dilution is carried out at an elevated temperature, which may be the reaction temperature. The organic solvent should be heated to an elevated temperature, as well, and the temperature of both the reaction mixture and the solvent should be in the range from about 70° C. to about 110° C. The most preferred solvent is acetonitrile.

The amount of organic solvent added is in the range from about 1 ml to about 5 ml per 1 gram of cytosine used. No particular holding period is required after dilution of the reaction mixture; the diluted mixture may be taken immediately to the next step. The diluted reaction mixture is added to a large amount of aqueous acid at an elevated temperature. The purpose of the aqueous acid is to dissolve the excess cytosine, which was used in the glycosylation reaction. Therefore, the amount and degree of acidity of the aqueous acid depends on the excess amount of cytosine used in the reaction itself. Further, the amount of aqueous acid also depends on the choice of acid substance used in preparing the aqueous acid.

The most preferred acid is hydrochloric acid, used at a concentration from about 1N to about 6N, most preferably at about 4N. When that acid is used, and the amount of excess cytosine is in the range from about 5× to about 20×, the amount of aqueous hydrochloric acid is from about 3 ml to about 5 ml per 1 gram of cytosine used.

However, other aqueous mineral acids and conditions are also usable and may be preferred in various circumstances. For example, mineral acid substances such as sulfuric acid, sulfurous acid, phosphoric acid, nitric acid, and phosphonic acid may be used if desired by the operator. The concentration of the acid can be varied rather widely, approximately in inverse proportion to the acceptable volume of the total isolation step. In general, concentrations from about 1N to about 10% can be used in the aqueous acid. The volume of aqueous acid must be optimized experimentally for the individual acid and the amount in the reaction mixture. The experiments needed are very simple, requiring the operator only to make successive adjustments of acid concentration and volume with the specific reaction mixture in use, observing the solubility of the cytosine in each case.

The aqueous acid need not be hot when it is combined with the reaction mixture. The aqueous acid may be at ambient temperature, so long as the complete mixture is warmed to a temperature in the range from about 70° C. to about 100° C. The heat of reaction may be sufficient to bring the mixture to that temperature, or it may be necessary in some cases to heat the mixture externally. When acetonitrile is used as the organic solvent, the most highly preferred temperature is from about 70° C. to about 80° C.

The acidic mixture resulting from addition of the diluted reaction mixture to the aqueous acid is held, preferably with moderate agitation, for a period of time. The physical changes which occur during this holding period are the dissolution of the excess cytosine in the aqueous acidic layer, and the precipitation of the desired beta-nucleoside. The precipitation is selective, and the undesired alpha-nucleoside remains in large part dissolved in the organic layer. Thus, the acidic mixture must be held, at about constant temperature, until those two physical changes have occurred. In general, a period of from about 10 minutes to about 1 hour is adequate.

After a sufficient holding period, the precipitated beta-nucleoside is separated from the two liquid phases by filtration or centrifugation, and is washed with additional aqueous acid. The filtration or centrifugation should be carried out at approximately constant temperature to prevent dissolved cytosine from precipitating out of solution. Beta-nucleoside isolated and purified in the above manner is of superior purity, with respect to alpha-nucleoside, cytosine and other impurities, and it is also found that the desired product is prepared in superior yield.

When the acidic mixture has been filtered or centrifuged to remove the solid product, the organic and aqueous layers of the filtrate are separated. The excess cytosine is in the aqueous layer and may be removed from that layer and recycled back into the process. Cytosine may be recovered simply by cooling the aqueous layer and filtering the precipitated cytosine, or by making the aqueous layer basic, cooling the basic solution, and filtering to collect the precipitated cytosine. Recovered cytosine from the above process is routinely recycled into the process, and, indeed, the cytosine used in Example 9 below was recovered from previous reaction mixtures.

The final phase of the reaction sequence is the removal of the protecting groups X, Z and/or W from the blocked nucleoside of formula I or IV. The same anomeric ratio of unprotected nucleoside is obtained by removal of the protecting groups.

Most silyl and silyl-amino protecting groups are easily cleaved by use of a protic solvent, such as water or an alcohol. The acyl protecting groups, such as benzoyl and the acyl-amino protecting groups, are removed by hydrolysis with a strong base at a temperature from about 0° C. to about 100° C. Strong or moderately strong bases suitable for use in this reaction are bases which have a pKa (at 25° C.) of about 8.5 to about 20.0. Such bases include alkali metal hydroxides such as sodium or potassium hydroxide; alkali metal alkoxides such as sodium methoxide or potassium t-butoxide; alkali metal amides; amines such as diethylamine, hydroxylamine, ammonia and the like; and other common bases such as hydrazine and the like. At least one equivalent of base is needed for each protecting group.

The acyl protecting groups can also be removed with acid catalysts, such as methanesulfonic acid, hydrochloric acid, hydrobromic acid, sulfuric acid, or with acidic ion exchange resins. It is preferred to carry out such hydrolysis at relatively high temperature, such as the reflux temperature of the mixture, but temperatures as low as ambient may be used when particularly strong acids are used.

The removal of ether protecting groups is carried out by known methods, for example, with ethanethiol and aluminum chloride.

The t-butyldimethylsilyl protecting group requires acid conditions, such as contact with gaseous hydrogen halide, for its removal.

Removal of the protecting groups may be conveniently carried out in alcoholic solvents, especially aqueous alkanols such as methanol. However, the deblocking reaction may also be carried out in any convenient solvent, such as polyols including ethylene glycol, ethers such as tetrahydrofuran, ketones such as acetone and methyl ethyl ketone, or dimethylsulfoxide.

In a preferred embodiment, the deblocking reaction employs ammonia to remove a benzoyl hydroxy-protecting group at a temperature of about 10° C. It is preferable, however, to use an excess of base in this reaction, although the amount of excess base used is not crucial.

The resulting beta- and alpha-anomer enriched nucleosides of formulas VI and VII may be extracted and/or isolated from the reaction mixture by the procedure described in U.S. Pat. No. 4,965,374, which is incorporated herein by reference.

The following examples illustrate specific aspects of the present invention and are not intended to limit the scope thereof in any respect and should not be so construed.

EXAMPLE 1

Preparation of beta-anomer enriched 1-(2'-deoxy-2',2'-difluoro-3',5'-di-O-benzoyl-D-ribofuranosyl)-4-aminopyrimidin-2-one with 10 equivalents of bis-trimethylsilylcytosine Bis-trimethylsilylcytosine was prepared by combining 2.44 g of cytosine, 5.15 ml of hexamethyldisilazane and 580 mg of ammonium sulfate with 5 ml of xylenes and refluxing the solution at 120° C. for 1 hour. An additional 5 ml of hexamethyldisilazane were added to form a homogenous solution which was refluxed for 30 minutes. The xylenes and excess hexamethyldisilazane were removed and a gelatin-like bis-trimethylsilylcytosine formed. 5.6 g of the bis-trimethylsilylcytosine were reconstituted in 20 ml of xylenes. The xylenes were removed and the bis-trimethylsilylcytosine was again reconstituted in 20 ml of xylenes. The bis-trimethylsilylcytosine was evaporated to dryness and reconstituted in 5 ml of xylenes. 1 g of 2-deoxy-2,2-difluoro-D-ribofuranosyl-3,5-dibenzoyl-1-α-methanesulfonate was reacted with the bis-trimethylsilylcytosine solution at 127° C. for 3.5 hours. HPLC analysis confirmed completion of the reaction.

To extract the nucleoside product, the reaction mixture was cooled to 60° C., diluted in 100 ml of ethyl acetate and washed with 200 ml of 1N hydrochloric acid. An emulsion occurred and the two layers that formed were separated. The organic layer was washed successively with 100 ml of 5% sodium bicarbonate, and 100 ml of saturated sodium chloride solution then dried over magnesium sulfate. A quantitative HPLC analysis of the ethyl acetate layer indicated that the yield of blocked beta-anomer nucleoside was 50 percent. The beta to alpha anomeric ratio of the blocked nucleoside was 2.2:1.

EXAMPLE 2

Preparation of beta-anomer enriched 1-(2'-deoxy-2',2'-difluoro-3',5'-di-O-benzoyl-D-ribofuranosyl)-4-aminopyrimidin-2-one with 5 equivalents of bis-trimethylsilylcytosine To 2.8 g of bis-trimethylsilylcytosine were added 3 ml of xylenes and the solution heated to 120° C. until the bis-trimethylsilylcytosine solubilized. 1 g of 2-deoxy-2,2-difluoro-D-ribofuranosyl-3,5-dibenzoyl-1-α-methanesulfonate, dissolved in 2 ml of xylenes, was heated and reacted with the bis-trimethylsilylcytosine solution at 130° C. for 16 hours. HPLC analysis confirmed completion of the reaction. The beta to alpha anomeric ratio of the blocked nucleoside was 1.1:1.

To extract the nucleoside product, the reaction mixture was diluted with 150 ml ethyl acetate and washed with 150 ml 1N hydrochloric acid. An emulsion occurred and the two layers that formed were separated. The organic layer was washed successively with 100 ml of water, and 100 ml of 5% sodium bicarbonate then dried over magnesium sulfate. For a more accurate HPLC analysis, 1 ml of the organic layer was evaporated to dryness and reconstituted in 1 ml of the acetonitrile. A quantitative HPLC analysis of the organic layer in acetonitrile indicated that the yield of blocked beta-anomer nucleoside was 36 percent.

EXAMPLE 3

Preparation of beta-anomer enriched 1-(2'-deoxy-2',2'-difluoro-3',5'-di-O-benzoyl-D-ribofuranosyl)-4-aminopyrimidin-2-one hydrochloride salt with 15 equivalents of bis-trimethylsilylcytosine Bis-trimethylsilylcytosine was prepared by combining 18.33 g of cytosine and 10 ml of anisole with 64.3 ml of N-methyl-N-(trimethylsilyl)-trifluoroacetamide and heating the solution at 80° C. for 30 minutes. 5.0 g of 2-deoxy-2,2-difluoro-D-ribofuranosyl-3,5-dibenzoyl-1-α-methanesulfonate, dissolved in 10 ml anisole, were reacted with the bis-trimethylsilylcytosine solution at 105° C. for 5 hours. HPLC analysis confirmed completion of the reaction. The beta to alpha anomeric ratio of blocked nucleoside was 5.4:1.

To isolate the nucleoside product, the reaction mixture was cooled to 60° C., diluted with 75 ml of ethyl acetate and washed with 200 ml of 1N hydrochloric acid. A semi-clear solution containing solid particulates formed. The solution

17 was warmed to 60° C.–70° C. for 15 minutes, filtered, and the isolated solid was washed successively with 20 ml of ethyl acetate then dried in a vacuum oven at 40° C. for 16 hours. The resulting nucleoside product weighed 4.0 g, m.p. 252° C.–256° C. A quantitative HPLC analysis confirmed that the product was the hydrochloride salt of the blocked beta-anomer nucleoside in a yield of 75 percent.

EXAMPLE 4

Preparation of alpha-anomer enriched 1-(2'-deoxy-2',2'-difluoro-3',5'-di-O-benzoyl-ribofuranosyl) -4-aminopyrimidin-2-one with 3 equivalents of bis-trimethylsilylcytosine Bis-trimethylsilylcytosine was prepared by the procedure described in Example 1, except 12.5 g of cytosine, 250 ml hexamethyldisilazane, 750 mg of ammonium sulfate and 40 ml anisole were used. The bis-trimethylsilylcytosine solution was heated to 125° C.–130° C. The solvents were removed after a homogenous solution was obtained and the resulting bis-trimethylsilylcytosine was reconstituted in 10 ml of anisole. 20 g of 2-deoxy-2,2-difluoro-D-ribofuranosyl-3,5-dibenzoyl-1-β-toluenesulfonate, dissolved in 30 ml anisole, were reacted with the bis-trimethylsilylcytosine solution at 115° C.–120° C. for 9 hours. HPLC analysis confirmed completion of the reaction. The alpha to beta anomeric ratio of the blocked nucleoside was 10:1.

To extract the nucleoside product, the reaction mixture was cooled to 60° C. diluted with 500 ml of ethyl acetate, and slowly added to 200 ml of 1N hydrochloric acid with agitation. As the solutions were combined, solids formed, therefore an additional 200 ml of ethyl acetate were added to solubilize the solids. An emulsion occurred and the two layers that formed were separated. The organic layer was washed successively with 200 ml of 5% sodium bicarbonate and 200 ml of water. After the solvent was evaporated from the organic layer, 15.6 g of blocked alpha-anomer nucleoside product were recovered. A quantitative HPLC analysis of the organic layer indicated that the yield of blocked alpha-anomer nucleoside was 88 percent.

EXAMPLE 5

Preparation of beta-anomer enriched 1-(2'-deoxy-2',2'-difluoro-3',5'-di-O-benzoyl-D-ribofuranosyl)-4-aminopyrimidin-2-one with 10 equivalents of bistrimethylsilylcytosine Bis-trimethylsilylcytosine was prepared by the procedure described in Example 1, except 20 g of cytosine, 380 ml of hexamethyldisilazane, 1.18 g of ammonium sulfate and 48 ml of xylenes were used. The bis-trimethylsilylcytosine was reconstituted in 24 ml xylenes. 9.6 g of 2-deoxy-2,2-difluoro-D-ribofuranosyl-3,5-dibenzoyl-1-toluenesulfonate, in a 70:30 alpha to beta ratio, were dissolved in 24 ml of xylenes and reacted with the bis-trimethylsilylcytosine solution for 1 hour. HPLC analysis confirmed completion of the reaction.

To extract the nucleoside product, the reaction mixture was cooled to 65° C. and 100 ml of ethyl acetate were added. The solution was maintained at 65° C. and washed with 200 ml of 1N hydrochloric acid. An emulsion occurred and the two layers that formed were separated. The organic layer washed with 200 ml of 5% sodium bicarbonate then dried over magnesium sulfate. The beta to alpha anomeric ratio of the blocked nucleoside was 1.1:1. A quantitative HPLC analysis indicated that the yield of blocked betaanomer nucleoside was 27 percent.

EXAMPLE 6

Preparation of beta-anomer enriched 1-(2'-deoxy-2',2'-difluoro-3',5'-di-O-benzoyl-D-ribofuranosyl)-4-aminopyrimidin-2-one with 20 equivalents of bis-trimethylsilylcytosine Bis-trimethylsilylcytosine was prepared by combining 30 g of cytosine with 175 ml of hexamethyldisilazane and 25 mg of ammonium sulfate under nitrogen and heating the solution at 120° C. for 2 hours. The mixture was cooled to 80° C. and diluted with 100 ml of ethyl acetate. The hexamethyldisilazane and ethyl acetate were subsequently atmospherically distilled at a temperature of 145° C. This procedure was repeated twice then the resulting bis-trimethylsilylcytosine was added to 15 ml of anisole and cooled to 110° C.–115° C. 5.75 g of 2-deoxy-2,2-difluoro-D-ribofuranosyl-3,5-dibenzoyl-1-α-methanesulfonate, dissolved in 10 ml of anisole, were stirred at 45° C. until a homogeneous solution formed and reacted with the bis-trimethylsilylcytosine solution at 115° C.–120° C. for 7 hours. HPLC analysis confirmed completion of the reaction. The beta to alpha anomeric ratio of blocked nucleoside was 7.3:1.

To isolate the nucleoside product, the reaction mixture was cooled to 88° C., diluted with 34 ml of ethyl acetate and washed with 125 ml of 4N hydrochloric acid. A slurry containing solid particulates formed and was stirred for 1 and ½ hours at 80° C. and filtered. The filtrate was washed with 50 ml of 4N hydrochloric acid and dried in a vacuum oven at 45° C. The resulting nucleoside product weighed 4.6 g. A quantitative HPLC analysis indicated that the yield of blocked beta-anomer nucleoside was 79.5 percent.

EXAMPLE 7

Preparation of beta-anomer enriched 1-(2'-deoxy-2',2'-difluoro-3',5'-di-O-benzoyl-D-ribofuranosyl)-4-aminopyrimidin-2-one hydrochloride salt with 20 equivalents of bis-trimethylsilylcytosine Bis-trimethylsilylcytosine was prepared by the procedure described in Example 6. The solution was cooled to 100° C. 5.75 g of 2-deoxy-2,2-difluoro-D-ribofuranose-3,5-dibenzoyl-1-α-methanesulfonate, dissolved in 10 ml of anisole, were stirred at 45° C. until a homogeneous solution formed and reacted with the bis-trimethylsilylcytosine solution at 110° C.–115° C. for 16 hours. HPLC analysis confirmed that only 3.9 percent of unreacted 2-deoxy-2,2-difluoro-D-ribofuranosyl-3,5-dibenzoate-1-α-methanesulfonate remained. The beta to alpha anomeric ratio of blocked nucleoside was 7.2:1.

To extract the nucleoside product, the reaction mixture was cooled and diluted with 69 ml off ethyl acetate at 65° C. The reaction mixture was then combined with 185 ml of 4N hydrochloric acid. The mixture was refluxed for 1 hour at 78° C. to form a slurry. The slurry was filtered and the solid was washed with 60 ml of 4N hydrochloric acid and dried in a vacuum oven at 45° C. The nucleoside product weighed 3.62 g. A quantitative HPLC analysis confirmed that the product was the hydrochloride salt of the blocked beta-anomer nucleoside in a yield of 64.2 percent.

EXAMPLE 8

Preparation of beta-anomer enriched 9-(2'-deoxy-2',2'-difluoro-3',5'-di-O-benzoyl-D-ribofuranosyl)-5-aminopurine with 15 equivalents of bis-trimethylsilyladenine Bis-trimethylsilyladenine was prepared by combining 7 g of adenine and 109 ml of hexamethyldisilazane with 250 mg of ammonium sulfate and heating the mixture at 110°–115° C. for 8 hours. The solution was refluxed for an additional 30 minutes and the excess hexamethyldisilazane subsequently removed and 14.5 g of the bis-trimethylsilyladenine were reconstituted in 3 ml of anisole. 1.58 g of 2-deoxy-2,2-difluoro-D-ribofuranosyl-3,5-dibenzoyl-1-α-methanesulfonate were reacted with the bis-trimethylsilyladenine solution at 105° C.–110° C. for 24 hours. HPLC analysis confirmed completion of the reaction.

To extract the nucleoside product, the reaction mixture was cooled to 30° C., diluted with 50 ml of ethyl acetate and washed with 75 ml of 4N hydrochloric acid. An emulsion occurred and the organic layer was separated and washed successively with 75 ml of 5% sodium bicarbonate, and 75 ml of saturated sodium chloride solution then dried over magnesium sulfate. The beta to alpha anomeric ratio of the blocked nucleoside was 6:1.

The following Table shows how the carbohydrate concentration and carbohydrate selected effects the anomeric ratio of the nucleoside product.

yields are based on the amount of carbohydrate and were calculated from a quantitative reverse phase HPLC analysis, wherein the corresponding solution product peak was compared with a standard, 1-(2'-deoxy-2',2'-difluoro-3',5'-di-O-benzoyl-β-D-ribofuranosyl)-4-aminopyrimidin-2-one, except in (a) which is an isolated product yield. (*) The carbohydrate concentration (Carbo. Conc.) has units of percent carbohydrate by weight (grams) per unit volume of solvent (milliliters). The nucleobase protecting group in each example is trimethylsilyl.

EXAMPLE 9

Preparation of beta-anomer enriched 1-(2'-deoxy-2',2'-difluoro-3',5'-di-O-benzoyl-D-ribofuranosyl)-4-aminopyrimidin-2-one with 22.5 equivalents of bis-trimethylsilylcytosine To a 250 ml 3-neck flask were added 30 g of cytosine, 25 mg of ammonium sulfate and 150 ml of hexamethyldisilazane, and the mixture was heated to 125° C. and held for 30 minutes after the dissolution of all of the solids. Then the temperature was raised to 145° C., held until boiling stopped, and then held to 120° C. under vacuum until solids began to form above the liquid level in the flask. Then the mixture was cooled to 105° C., and 25 ml of anisole was added.

In another 125 ml flask were combined 10 ml of anisole and 5.75 g of 2-deoxy-2,2-difluoro-3,5-dibenzoyl-D-ribo-

TABLE

| Example | Solvent | Carbo. | Base (R') | Base (R') Equiv. | Temp. | Carbo. Conc. | α/β Nucleoside Ratio | Yield |
|---------|---------|--------|-----------|------------------|-------|--------------|----------------------|-------|
|         | Xylenes | α-OMs  | Cytosine  | 1.5 | 127° C. | 20% | 1.5:1 | 14% β |
|         | Xylenes | α-OMs  | Cytosine  | 1.5 | 127° C. | 50% | 1.5:1 | 15% β |
| 2       | Xylenes | α-OMs  | Cytosine  | 5   | 130° C. | 20% | 1:1.1 | 36% β |
| 1       | Xylenes | α-OMs  | Cytosine  | 10  | 127° C. | 50% | 1:2.2 | 50% β |
|         | Xylenes | α-OMs  | Cytosine  | 10  | 120° C. | 20% | 1:1.6 | 32% β |
|         | Xylenes | 50:50 α/β-OMs | Cytosine | 1.5 | 125° C. | 50% | 3:1 | 12% β |
|         | Anisole | α-OMs  | Cytosine  | 2   | 105° C. | 20% | 1.3:1 | 18% β |
|         | Anisole | α-OMs  | Cytosine  | 3   | 105° C. | 50% | 1:1.3 | 22% β |
| 3       | Anisole | α-OMs  | Cytosine  | 15  | 105° C. | 50% | 1:5.4 | 75% β(a) |
|         | Anisole | α-OMs  | 5-F-Cytosine | 10 | 115° C. | 50% | 1:6 | N/D |
|         | Anisole | α-OMs  | 5-F-Uracil | 5  | 130° C. | 50% | 1:6 | N/D |
|         | Xylenes | β-OTs  | Cytosine  | 5   | 120° C. | 50% | 7.8:1 | 73% α |
| 4       | Anisole | β-OTs  | Cytosine  | 3   | 115° C. | 50% | 10:1 | 88% α |
|         | Anisole | α-OTs  | Cytosine  | 3   | 115° C. | 50% | 6:1 | 47% α |
|         | Xylenes | 70:30 α:β-OTs | Cytosine | 3 | 123° C. | 20% | 1.7:1 | 6% β |
|         | Xylenes | 70:30 α:β-OTs | Cytosine | 5 | 125° C. | 20% | 1.7:1 | N/D |
| 5       | Xylenes | 70:30 α:β-OTs | Cytosine | 10 | 125° C. | 20% | 1:1.1 | 27% β |
|         | Xylenes | 70:30 α:β-OTs | Cytosine | 10 | 125° C. | 20% | 1.3:1 | 23% β |
|         | Xylenes | 85:15 α:β-OBs | N-Acetyl-Cytosine | 5 | 110° C. | 20% | 1:1 | N/D |
| 6       | Anisole | α-OMs  | Cytosine  | 20  | 115° C. | 25% | 1:7.3 | 79.5% β(a) |
|         | Anisole | α-OMs  | Adenine   | 15  | 110° C. | 50% | 1:6 | N/D |
| 7       | Anisole | α-OMs  | Cytosine  | 20  | 115° C. | 25% | 1:7.2 | 64% β |

(N/D) means not determined. The carbohydrates (Carbo.) are hydroxy protected and include (α- or β-OMs is alpha- or beta- 2,2-difluoro-2-deoxy-D-ribofuranosyl-3,5-dibenzoyl-1-methanesulfonate; β- or α-OTs is Beta 2,2-difluoro-2-deoxy-D-ribofuranosyl-3,5-dibenzoyl-1-toluenesulfonate; and α- or β-OBs is alpha-or beta-2,2-difluoro-2-deoxy-D-ribofuranosyl-3,5-dibenzoyl-1-bromo-benzenesulfonate. The 70:30 α:β-OTs carbohydrates were obtained by anomerizing β-OTs with a salt of p-toluenesulfonic acid. The furanosyl-1-α-methanesulfonate, and the mixture was heated until a homogeneous liquid was formed. That liquid was added at constant temperature to the cytosine mixture, and the combined mixture was held at 100° C. for 24 hours.

A 133 ml portion of 4N hydrochloric acid was placed in a 500 ml flask. A 31.3 ml portion of acetonitrile was added to the reaction mixture, and the diluted reaction mixture was then poured onto the acid with constant stirring, while a cooling bath was applied to the 500 ml flask. The combined mixture was then stirred at 70° C. for 10 minutes, and was then filtered at constant temperature. The wet cake was then slurried for 10 minutes at 70° C. with 25 ml of 4N hydrochloric acid, and was filtered again. That filter cake was slurried again at 70° C. with 50 ml of minutes at 70° C. with 25 ml of deionized water, filtered, and the wet cake was slurried again at 70° C. with 50 ml of deionized water. The pH of the aqueous slurry was raised to 7 with sodium bicarbonate, and the mixture was stirred for 10 minutes at 50° C. or above, and was filtered again. That filter cake was slurried once more with 50 ml of deionized water at 70° C. for 10 minutes, filtered, and the filter cake was dried and analyzed. It weighed 3.98 g, representing an isolated yield of 61 percent, and contained less than 1 percent of the undesired alpha-anomer.

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. A stereoselective glycosylation process for preparing a beta-anomer enriched nucleoside of the formula

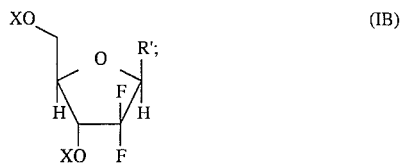

wherein each X is independently selected from hydroxy protecting groups and R' is a nucleobase selected from the group consisting of

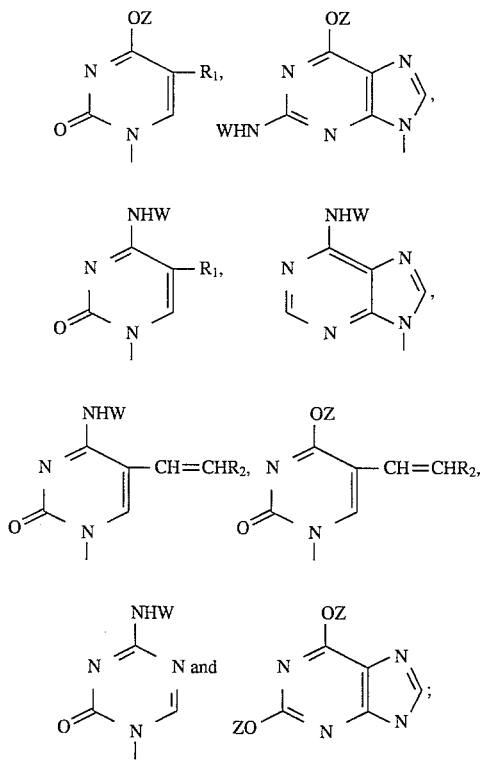

wherein $R_1$ is selected from the group consisting of hydrogen, alkyl and halo; $R_2$ is selected from the group consisting of hydrogen, alkyl and halo; Z is a hydroxy protecting group; and W is an amino protecting group; comprising reacting a concentrated alpha-anomer enriched 2,2-difluorocarbohydrate of the formula

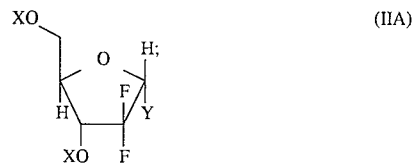

wherein Y is selected from the group consisting of alkylsulfonyloxy, arylsulfonyloxy, substituted alkylsulfonyloxy and substituted arylsulfonyloxy, wherein substituted refers to a substitution by one or more of the groups selected from cyano, halo, carboalkoxy, toluoyl, nitro, alkoxy, alkyl and dialkylamino and each X is as defined above; with at least a molar equivalent of a nucleobase derivative, R", selected from the group consisting of

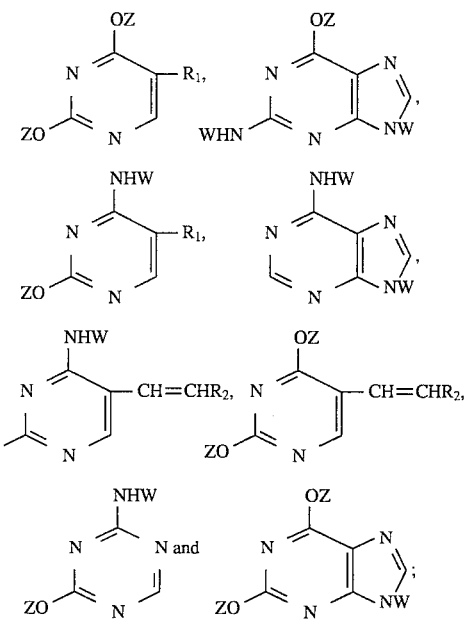

wherein $R_1$, $R_2$, Z and W are as defined above; in a high boiling inert solvent.

2. The process of claim 1 wherein the carbohydrate concentration is about 20 percent to about 70 percent.

3. The process of claim 1 wherein the amount of R" is from about 3 molar equivalents to about 30 molar equivalents.

4. The process of claim 1 wherein Y is selected from the group consisting of methanesulfonyloxy, 2-chloroethanesulfonyloxy, toluenesulfonyloxy, p-nitrobenzenesulfonyloxy, 2,4-dinitrobenzenesulfonyloxy and p-bromobenzenesulfonyloxy.

5. The process of claim 1 wherein X is selected from the group consisting of mono-substituted benzoyl, di-substituted benzoyl and benzoyl, wherein substituted refers to a substitution by one or more of the groups selected from cyano, halo, carboalkoxy, toluoyl, nitro, alkoxy, alkyl, and dialkylamino.

6. The process of claim 1 wherein Z and W are selected from the group consisting of trialkylsilyl, t-butoxycarbonyl, benzyloxycarbonyl, 4-methoxybenzyloxycarbonyl, 4-nitrobenzyloxycarbonyl, formyl and acetyl.

7. The process of claim 1 wherein the solvent is selected from the group consisting of aromatic, haloalkyl, alkoxy- and halo-substituted aromatic solvents and mixtures thereof.

8. The process of claim 7 wherein the solvent is selected from the group consisting of toluene, xylenes, 1,2-dichloroethane, 1,1,2-trichloroethane, glyme, diglyme, dichlorobromomethane, dibromochloromethane, tribromomethane, dibromomethane, anisole, and mixtures thereof.

9. The process of claim 1 wherein the reaction temperature is from about 70° C. to about 170° C.

10. The process of claim 1 wherein R" is of the formula

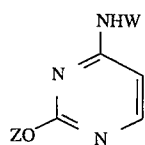

wherein Z and W are trimethylsilyl.

11. The process of claim 10 wherein the carbohydrate concentration is from about 30 percent to about 50 percent.

12. The process of claim 11 wherein the amount of R' is from about 15 molar equivalents to about 20 molar equivalents.

13. The process of claim 12 wherein Y is methanesulfonyloxy.

14. The process of claim 11 wherein X is benzoyl.

15. The process of claim 14 wherein the solvent is selected from the group consisting of toluene, xylenes, and anisole, and mixtures thereof.

16. The process of claim 15 wherein the reaction temperature is from about 100° C. to about 130° C.

17. A stereoselective glycosylation process for preparing an alpha-anomer enriched nucleoside of the formula

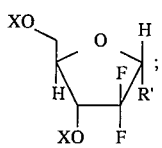 (IA)

wherein each X is independently selected from hydroxy protecting groups; and R' is a nucleobase selected from the group consisting of

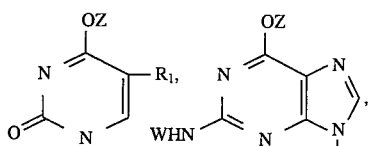

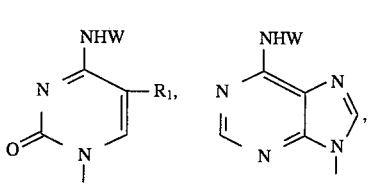

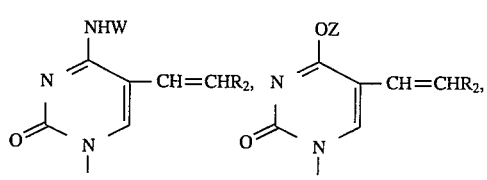

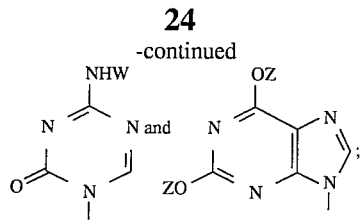

wherein $R_1$ is selected from the group consisting of hydrogen, alkyl and halo; $R_2$ is selected from the group consisting of hydrogen, alkyl and halo; Z is a hydroxy protecting group; and W is an amino protecting group; comprising reacting a concentrated beta-anomer enriched 2,2-difluorocarbohydrate of the formula

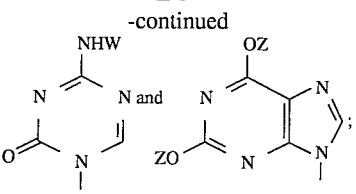 (IIB)

wherein Y is selected from the group consisting of arylsulfonyloxy and substituted arylsulfonyloxy, wherein substituted refers to a substitution by one or more of the groups selected from cyano, halo, carboalkoxy, toluoyl, nitro, alkoxy, alkyl, and dialkylamino and each X is as defined above; with at least a molar equivalent of a nucleobase derivative, R", selected from the group consisting of

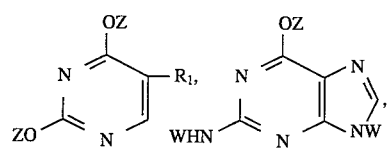

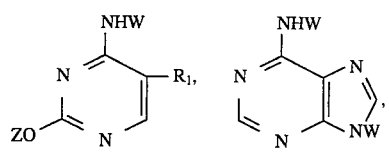

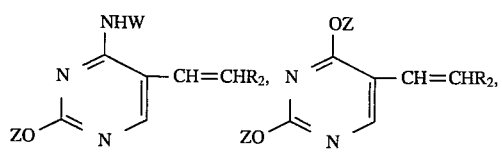

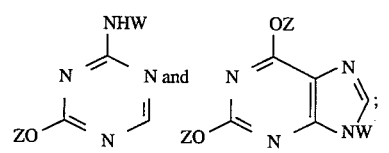

wherein $R_1$, $R_2$, Z and W are as defined above; in a high boiling inert solvent.

18. A stereoselective glycosylation process for preparing a beta-anomer enriched nucleoside of the formula

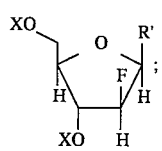 (IVB)

wherein each X is independently selected from hydroxy protecting groups and R' is a nucleobase selected from the group consisting of

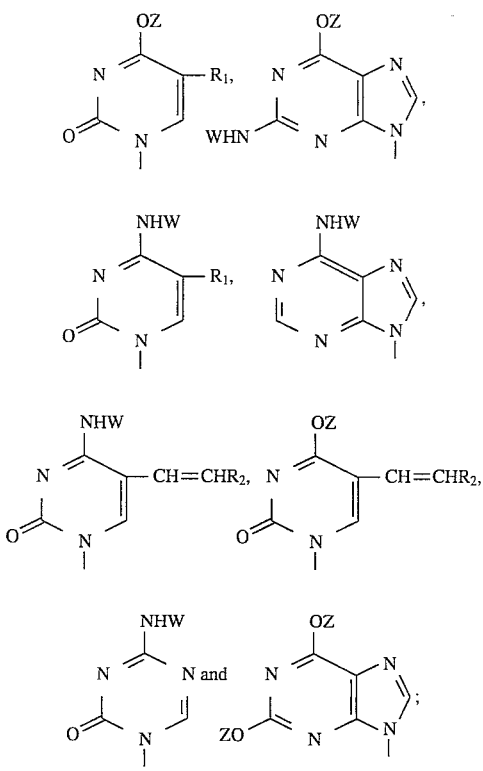

wherein $R_1$ is selected from the group consisting of hydrogen, alkyl and halo; $R_2$ is selected from the group consisting of hydrogen, alkyl and halo; Z is a hydroxy protecting group; and W is an amino protecting group; comprising reacting a concentrated alpha-anomer enriched 2-fluorocarbohydrate of the formula

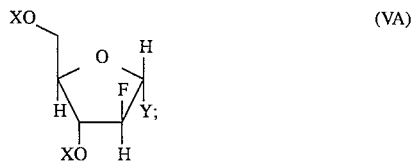

wherein Y is selected from the group consisting of alkylsulfonyloxy, arylsulfonyloxy, substituted alkylsulfonyloxy and substituted arylsulfonyloxy, wherein substituted refers to a substitution by one or more of the groups selected from cyano, halo, carboalkoxy, toluoyl, nitro, alkoxy, alkyl, and dialkylamino and each X is as defined above; with at least a molar equivalent of a nucleobase derivative, R", selected from the group consisting of

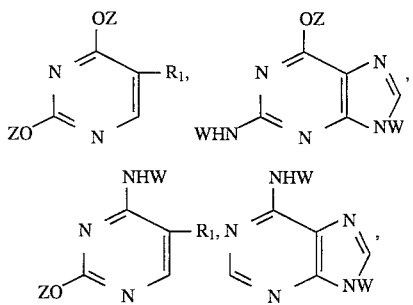

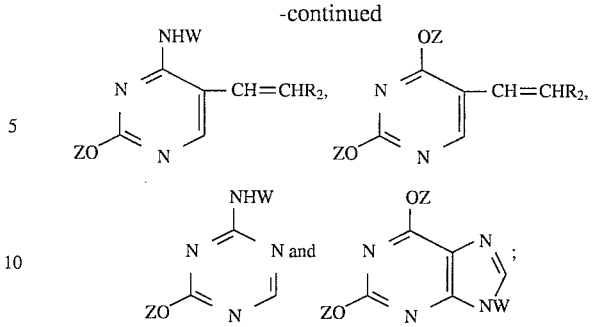

wherein $R_1$, $R_2$, Z and W are as defined above; in a high boiling inert solvent.

19. The process of claim 18 wherein the carbohydrate concentration is about 20 percent to about 70 percent.

20. The process of claim 18 wherein the amount of R" is from about 3 molar equivalents to about 30 molar equivalents.

21. The process of claim 18 wherein Y is selected from the group consisting of methanesulfonyloxy, 2-chloroethanesulfonyloxy, toluenesulfonyloxy, p-nitrobenzenesulfonyloxy, 2,4-dinitrobenzenesulfonyloxy and p-bromobenzenesulfonyloxy.

22. The process of claim 18 wherein X is selected from the group consisting of mono-substituted benzoyl, disubstituted benzoyl and benzoyl, wherein substituted refers to a substitution by one or more of the groups selected from cyano, halo, carboalkoxy, toluoyl, nitro, alkoxy, alkyl, and dialkylamino.

23. The process of claim 18 wherein Z and W are selected from the group consisting of trialkylsilyl, t-butoxycarbonyl, benzyloxycarbonyl, 4-methoxybenzyloxy-carbonyl, 4-nitrobenzyloxycarbonyl, formyl and acetyl.

24. The process of claim 18 wherein the solvent is selected from the group consisting of aromatic, haloalkyl, alkoxy- and halo-substituted aromatic solvents and mixtures thereof.

25. The process of claim 24 wherein the solvent is selected from the group consisting of toluene, xylenes, 1,2-dichloroethane, 1,1,2-trichloroethane, glyme, diglyme, dichlorobromomethane, dibromochloromethane, tribromomethane, dibromomethane, anisole, and mixtures thereof.

26. The process of claim 18 wherein the reaction temperature is from about 70° C. to about 170° C.

27. A stereoselective glycosylation process for preparing an alpha-anomer enriched nucleoside of the formula

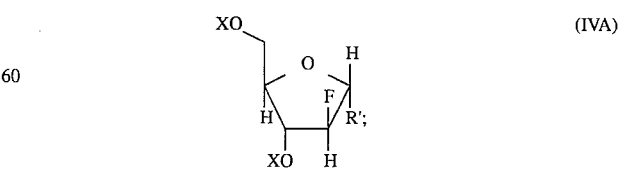

wherein each X is independently selected from hydroxy protecting groups; and R' is a nucleobase selected from the group consisting of

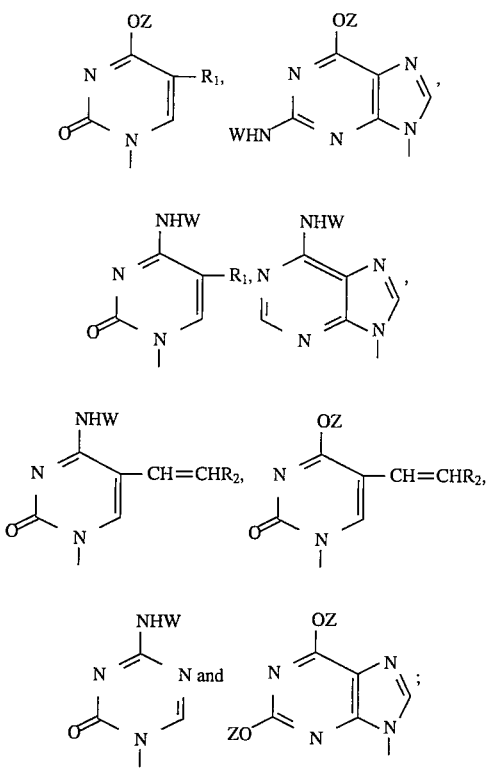

wherein $R_1$ is selected from the group consisting of hydrogen, alkyl and halo; $R_2$ is selected from the group consisting of hydrogen, alkyl and halo; Z is a hydroxy protecting group; and W is an amino protecting group; comprising reacting a concentrated beta-anomer enriched 2-fluorocarbohydrate of the formula

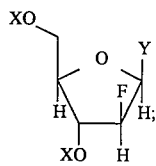 (VB)

wherein Y is selected from the group consisting of arylsulfonyloxy and substituted arylsulfonyloxy, wherein substituted refers to a substitution by one or more of the groups selected from cyano, halo, carboalkoxy, toluoyl, nitro, alkoxy, alkyl, and dialkylamino and each X is as defined above; with at least a molar equivalent of a nucleobase derivative, R", selected from the group consisting of

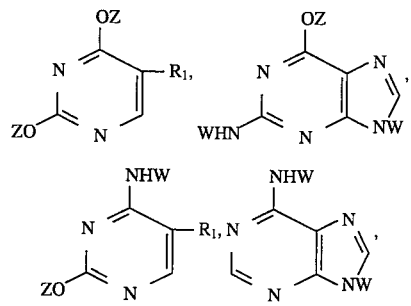

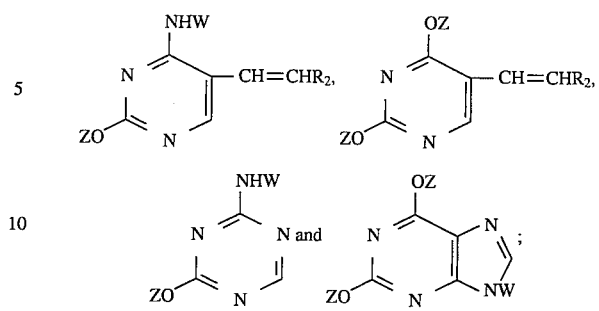

wherein $R_1$, $R_2$, Z and W are as defined above; in a high boiling inert solvent.

28. The process of claim 1 further comprising deblocking to form a beta-anomer enriched nucleoside of the formula

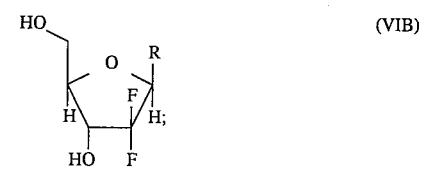 (VIB)

wherein R is a deblocked nucleobase selected from the group consisting of

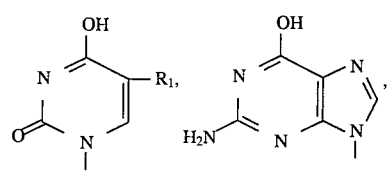

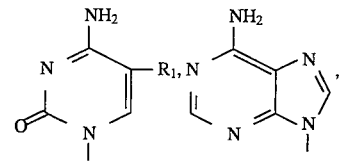

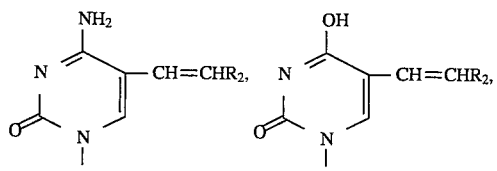

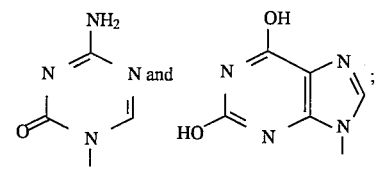

wherein $R_1$ is selected from the group consisting of hydrogen, alkyl and halo; and $R_2$ is selected from the group consisting of hydrogen, alkyl and halo.

29. The process of claim 28 wherein R is of the formula

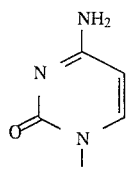

30. The process of claim 17 further comprising deblocking to form an alpha-anomer enriched nucleoside of the formula

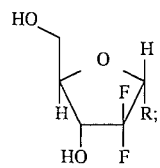 (VIA)

wherein R is a deblocked nucleobase selected from the group consisting of

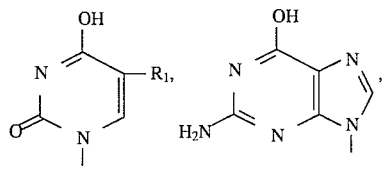

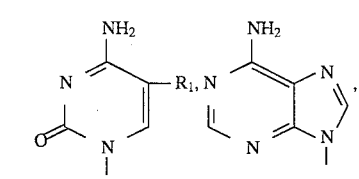

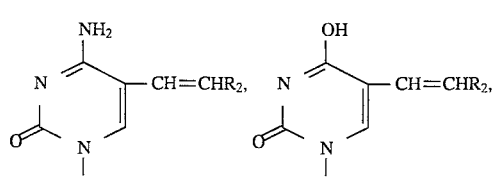

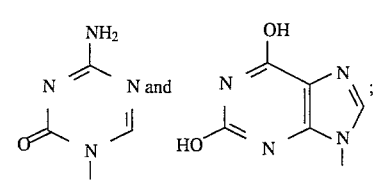

wherein $R_1$ is selected from the group consisting of hydrogen, alkyl and halo; and $R_2$ is selected from the group consisting of hydrogen, alkyl and halo.

31. The process of claim 18 further comprising deblocking to form a beta-anomer enriched nucleoside of the formula

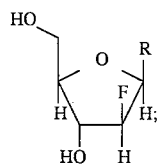 (VIIB)

wherein R is a deblocked nucleobase selected from the group consisting of

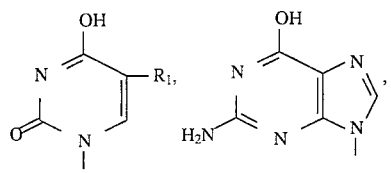

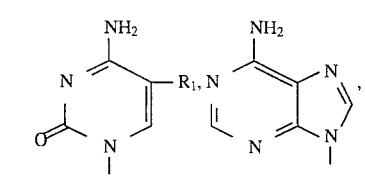

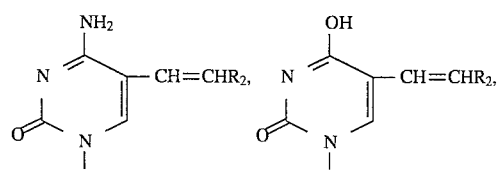

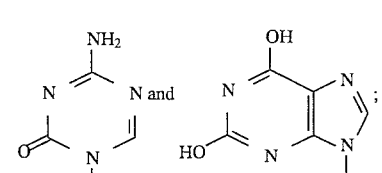

wherein $R_1$, is selected from the group consisting of hydrogen, alkyl and halo; and $R_2$ is selected from the group consisting of hydrogen, alkyl and halo.

32. A process of claim 27 further comprising a deblocking to form an alpha-anomer enriched nucleoside of the formula

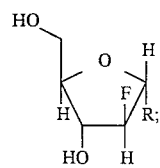 (VIIA)

wherein R is a deblocked nucleobase selected from the group consisting of

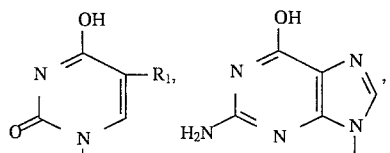

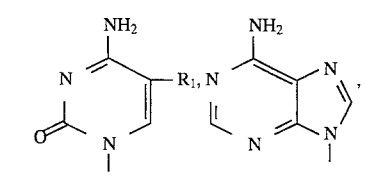

-continued

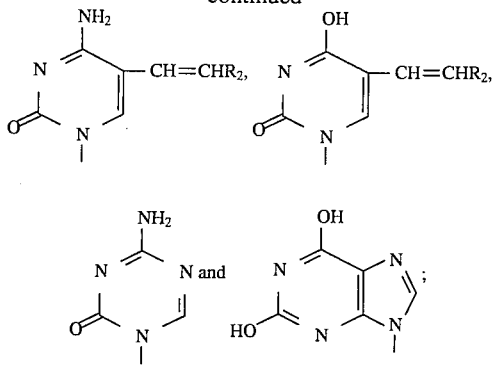

wherein $R_1$ is selected from the group consisting of hydrogen, alkyl and halo; and $R_2$ is selected from the group consisting of hydrogen, alkyl and halo.

33. A process of claim 10 wherein the product of formula IB is isolated and purified by 1) diluting the reaction mixture with an organic solvent Selected from the group consisting of acetonitrile, ethyl acetate and tetrahydrofuran, wherein the amount of said organic solvent added ranges from about 1 ml to about 5 ml per 1 gram of cytosine;

2) adding the diluted reaction mixture to a sufficient amount of aqueous acid with said sufficient amount being enough aqueous acid to dissolve the excess cytosine;

3) holding the acid mixture so prepared at a temperature from about 70° C. to about 100° C. until the product of formula IB has precipitated; and 4) separating the solid product.

34. A process of claim 33 wherein the reaction mixture is diluted with acetonitrile.

35. A process of claim 33 wherein the aqueous acid is hydrochloric acid from about 1N to about 6N.

36. A process of claim 33 wherein the acid mixture is agitated while the product is precipitating.

37. A process of claim 33 further including deblocking to form the nucleoside which is 1-(2'-deoxy-2',2'-difluoro-D-ribofuranosyl-4-aminopyrimidin-2-one.

38. The process of claim 33 further including recovering said excess cytosine.

* * * * *